United States Patent [19]

Fotheringham et al.

[11] Patent Number: 5,120,837

[45] Date of Patent: Jun. 9, 1992

[54] DNA ENCODING PHE A FEEDBACK INHIBITION RESISTANT ENZYME ANALOGUES

[75] Inventors: Ian G. Fotheringham, Wheeling; Jennifer Nelms, Des Plaines, both of Ill.

[73] Assignee: The NutraSweet Company, Deerfield, Ill.

[21] Appl. No.: 409,769

[22] Filed: Sep. 20, 1989

[51] Int. Cl.$^5$ .............................................. C07H 21/02
[52] U.S. Cl. .................................... 536/27; 536/28; 536/29
[58] Field of Search ............................ 536/27, 28, 29

[56] References Cited

PUBLICATIONS

Todd et al., Journal of Bacteriology, 167 (1), 257–264 (1986).
Miura et al., Gene, 38, 271–274 (1985).
Shioda et al., Nucleic Acids Research, 14 (4), 1545–1563 (1986).
Glaser et al., The EMBO Journal, 7(12), 3997–4004 (1988).
Hudson et al., J. Mol. Biol. 180, 1023–1051 (1984).

Primary Examiner—Johnnie R. Brown
Assistant Examiner—L. Eric Crane
Attorney, Agent, or Firm—Marshall, O'Toole, Gerstein, Murray & Bicknell

[57] ABSTRACT

Disclosed are DNA sequences bonding deletion, substitution and/or addition analogs of the *E. coli* enzyme, chorismate mutase/prephenate dehydratase (CMPD). Preferred expression products include [des-Gln$^{307}$, des-Ala$^{308}$, des-Gly$^{309}$, des-Ala$^{310}$]CMPD; [Leu$^{306}$]CMPD; [des-Thr$^{304}$, Lys$^{305}$, des-Gln$^{306}$]CMPD; and [Cys$^{309}$]CMPD display enzymatic activity of the wild type enzyme but are more resistant to inhibition in the presence of phenylalanine.

4 Claims, 1 Drawing Sheet

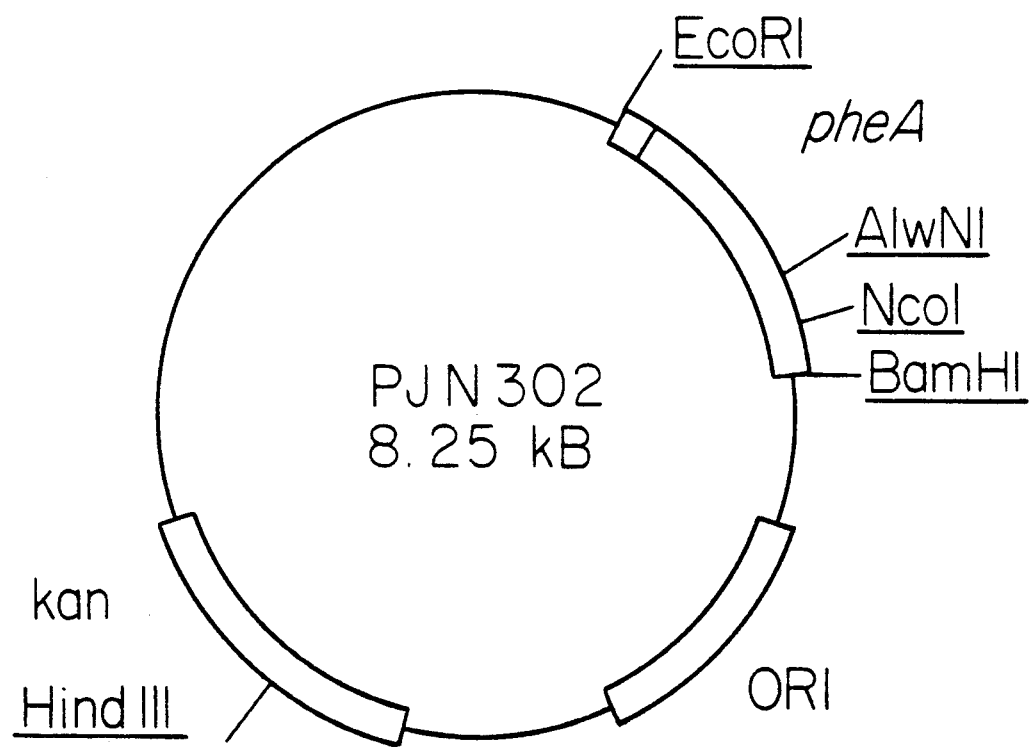

5,120,837

DNA ENCODING PHE A FEEDBACK INHIBITION RESISTANT ENZYME ANALOGUES

BACKGROUND

The present invention relates generally to the microbial synthesis of phenylalanine and more particularly to novel DNA sequences encoding polypeptide analogs of the E. coli enzyme, chorismate mutase/prephenate dehydratase. In comparisons to the wild type enzyme, the enzymatic activities of the analogs are more resistant to feedback inhibition by phenylalanine. The analog-encoding DNA sequences are therefore useful in supplementing the enzymatic wherewithal of microorganisms employed in phenylalanine production.

In the microbial production of L-phenylalanine in E. coli numerous metabolic enzymes are involved. Among the most significant of these is a bifunctional enzyme, chorismate mutase/prephenate dehydratase (CMPD), which is involved in both the conversion of chorismate to prephenate and prephenate to phenylpyruvate. CMPD has been determined to be the expression product of the E. coli pheA gene, the nucleotide sequence of which has been reported by Hudson et al., *J. Mol. Biol.*, 180, 1023-1051 (1984).

CMPD has been proposed to function enzymatically in a dimeric form comprising two identical polypeptide products of pheA gene expression. The enzyme is subject to "feedback inhibition" of its activities by the metabolic pathway end product, L-phenylalanine. When phenylalanine levels approach 1.0 mM, for example, there is a dramatic slowdown in prephenate dehydratase activity, probably due to participation of phenylalanine in the reversible formation of enzymatically inactive CMPD polypeptide tetramers. [See, e.g., Baldwin et al., *Arch. Biochem. Biophys.*, 211, 66-75 (1981)] At phenylalanine concentrations of about 1.0 mM, prephenate dehydratase activity is reduced by at least 90 percent.

With the advent of recombinant technologies for the cloning and expression of genes, attempts have been made to augment the endogenous CMPD capacity of E. coli host cells employed in phenylalanine production [Forberg et al., *J. Biotech.*, 7, 319-332 (1988); Choi et al., *Biotechnol. Lett.*, 8, 223-228 (1982); Hwang et al., *Appl. Microbiol. Biotechnol.*, 22, 108-113 (1985); Gil et al., *Enzyme Microb. Technol.*, 7, 370-372 (1985); Park et al., *Chem. Eng. Commun.*, 45, 185-196 (1986)].

Mutant E. coli strains have been reported to produce CMPD enzyme substantially free of phenylalanine feedback inhibition. See, e.g., Tribe, Published Australian Application No. 72727/81.

Backmann et al., U.S. Pat. No. 4,753,883, reports that transformation of host cells with "mutant" DNA sequences encoding CMPD analog polypeptides which are less sensitive to phenylalanine inhibition on the basis that ". . . the catalytically critical segment of E. coli CMPD lies within its N-terminal 337 amino acids, that phenylalanine feedback sensitivity depends on a single amino acid tryptophan 338, and that deletion of the entire 49 C-terminal amino acids does not destroy catalytic activity but does substantially destroy feedback sensitivity". Backmann et al. proposes the development of plasmid vectors incorporating DNA sequences encoding CMPD Trp$^{338}$ deletion as well as substitution analogs involving Trp$^{338}$ and the use of such plasmid vectors to transform microbial hosts for phenylalanine production.

BRIEF SUMMARY

The present invention provides novel DNA sequences encoding for E. coli CMPD analog polypeptides whose prephenate dehydratase and/or chorismate mutase enzymatic activities are less sensitive to inhibition by the presence of phenylalanine than are the wild type E. coli CMPD enzyme. The present invention also provides the polypeptides encoded by these sequences. DNA sequences according to the present invention include those encoding deletion, substitution and/or addition analogs affecting residues 301 to 315, and preferably residues 304 to 310, of E. coli CMPD. Presently preferred analog-encoding sequences specify the following polypeptides wherein and hereinafter "des" identifies a deletion or lack of the residue with which it is associated: [des-Gln$^{307}$, des-Ala$^{308}$, des-Gly$^{309}$, des-Ala$^{310}$]CMPD; [Leu$^{306}$]CMPD; [des-Thr$^{304}$, Lys$^{305}$, des-Gln$^{306}$]CMPD; and [Cys$^{309}$]CMPD. The expression products of each of these analog-encoding DNA sequences display both prephenate dehydratase and chorismate mutase activity but one or both of the enzymatic activities for these products is less sensitive to inhibition by the presence of phenylalanine. Preferred for its resistance to inhibition of prephenate dehydratase activity by 100 mM concentration phenylalanine is the expression product of the [des-Thr$^{304}$, Lys$^{305}$, des-Gln$^{306}$]CMPD-encoding DNA sequence. Preferred for its resistance to inhibition of chorismate mutase activity is [Cys$^{209}$]CMPD.

Also provided by the present invention are autonomously replicating DNA expression vectors comprising DNA sequences of the invention operatively associated with expression control DNA sequences (promoters, operators, and the like) facilitating expression (transcription and translation) of the desired CMPD analog polypeptides in a selected host cell, e.g., E. coil, transformed therewith, Preferred expression vectors comprise a selectable marker gene for use in confirming host cell transformation and include a promoter having expression control DNA sequences modified between EcoRI and HaeII sites as indicated in Example 1 and derived from those operatively associated with the endogenous expression of wild type E. coli CMPD enzyme (e.g., the expression control sequences of the E. coli pheA gene).

While preferred prototypical E. coli CMPD analog-encoding DNA sequences of the present invention were developed by chemical mutagenesis performed on a vector incorporating the wild type E. coli pheA gene, it is consistent with the present invention to hereafter affect formation of DNA sequences according to the invention by site-directed mutagenesis (performed, e.g., on the wild type pheA gene) as well as through the manufacture by chemical synthesis of part or all of the CMPD polypeptide-encoding sequence.

DNA sequences of the invention encoding deletion analogs of CMPD lack from one to fifteen codons specifying residues within the region spanning amino acid residues at positions 301 through 315 in the amino acid sequence of the wild type enzyme. Deletions may be continuous or discontinuous and are preferably made in the region spanning the base pairs encoding amino acid residues 304 through 310. Substitution analog-encoding DNA sequences according to the invention include those wherein from one to three base pairs within codons specifying one or more of residues at positions 301 through 315 (and preferably residues 304 through 310) in the amino acid sequence of CMPD are changed in a manner allowing for the expression at the position where the change is made of an amino acid other than one present in the wild type enzyme. Addition analog-encoding DNA sequences correspondingly include additional codons for additional residues in the above-noted regions of the enzyme. Presently preferred are those DNA sequences encoding deletion analog polypeptides, substitution analog polypeptides and polypeptide analogs involving both deletions and substitutions in the wild type CMPD amino acid sequence. It is also within the contemplation of the invention that the above-noted modifications be "combined" with other known and later developed DNA sequence modifications which allow for expression of CMPD polypeptide analogs displaying enhanced chorismate mutase and/or prephenate dehydratase activity or further enhanced phenylalanine feedback inhibition resistance.

DNA sequences of the invention have manifest utility when transformed into a suitable *E. coli* host (by means of a vector or use of chromosomal insertion techniques) for the purpose of enhancing cellular capacity to effect synthesis of phenylalanine.

Other aspects and advantages of the present invention will be apparent upon consideration of the detailed description of preferred embodiments thereof.

BRIEF DESCRIPTION OF THE DRAWING

The FIGURE is a restriction map of a plasmid, pJN302, including pheA DNA.

DETAILED DESCRIPTION

The following illustrative examples relate to the development of presently preferred DNA sequences of the invention. More specifically, Example 1 relates to development of analog-encoding DNA sequences by chemical mutation; Example 2 provides the results of phenylalanine feedback inhibition screening; and Example 3 relates to sequence analysis performed on DNA sequence developed in Example 1.

EXAMPLE 1

Chemical mutagenesis was carried out on plasmid pJN302. Plasmid pJN302 consists of the vector pLG338 carrying an EcoRI to BamHI insert comprising the pheA gene of *E. coli* K12. The pheA gene has been modified to remove regulatory sequences associated with the promoter and to insert a BamHI site downstream of the coding sequence. The pheA gene encodes the wild type CMPD.

The pheA gene may be isolated from the chromosome of *E. coli* K12 on a 6.3 kb EcoRI to BamHI fragment as described both in Edwards et al., PCT Publication No. WO 87/00202 (incorporated by reference herein) and Hudson et al., *J. Mol. Biol.*, 180, 1023-1051 (1984). Following determination of the nucleotide sequence of the pheA gene and its flanking regions a BamHI restriction site may be introduced immediately downstream of the gene by converting the sequence GGTGCC to GGATCC by site directed mutagenesis as illustrated in Edwards et al., PCT Publication No. WO 87/00202. This sequence starts at the 7th nucleotide following the TGA stop codon of the pheA gene as follows.

Val Asp Pro Thr Stop       <u>BamHI</u>
GTT GAT CCA ACC TGA TGA AAA<u>GGATCC</u>GGATG The promoter region of the pheA gene may be deregulated by replacing the promoter and attenuator sequences with a synthetic promoter based upon the natural promoter but lacking the dyad symmetry overlapping the Pribnow sequence (−10). This replacement may be made between the EcoRI site upstream of the gene and a HaeII site within the N-terminus of the natural pheA gene. The nucleotide sequence of the synthetic replacement region may be:

<u>EcoRI</u>                         −35                       −10
G<u>AATTC</u>TTTTTTG<u>TTGACA</u>GCGTGAAAACA GTACGGG<u>TATAAT</u>ACTAAA

S.D.              start                       <u>HaeII</u>
GTCACAAA<u>AAGG</u>CAACACT<u>ATG</u>ACATCGGA AAACCCGTTA CT<u>GGCGCT</u>

The terminal restriction sites are underlined, as are the −35 and −10 regions of the promoter and the ribosome binding site (S.D. followed by ATG start codon). The pheA gene may be isolated from the constructions described in Edwards et al. by BamHI and EcoRI cleavage at the upstream EcoRI site and the downstream BamHI site and EcoRI/BamHI may be cloned into EcoRI- and BamHI-cleaved pLG338 [Stoker et al., Gene, 18, 335-341 (1982)] to generate pJN302, a restriction map of which is illustrated in the FIGURE pLG338 is readily available from many labs including the lab of Stoker et al.

Approximately 2 μg of pJN302 DNA was combined in a 200 μl reaction mixture with 50 mM sodium acetate pH 4.6, 88 mM sodium nitrite and 0.25 mM Spermine. The reaction mixture was incubated at 30° C. and a 60 μl sample removed after 30 minutes. The sample was placed into 30 μl of 1 M Tris at pH 8. To this was added 4.5 μl of 4 M NaCl and 300 μl of ethanol. The DNA was then precipitated at −20° C. for 4 hours and recovered by centrifugation in an Eppendorf microfuge. A further sample of 70 μl was taken at 60 minutes and to this was added 35 μl of 1M Tris pH 8. A further 5.25 μl of 4M NaCl was then added and 350 μl of ethanol. The DNA was precipitated and recovered as before. The remaining 70 μl of reaction mixture was removed after a total of 90 minutes incubation and treated exactly as the 60 minute sample.

DNA pellets were resuspended in 10 μl of water and 3 μl of each was used to transform competent cells of bacterial strain HW1012 (pheA). Transformants were isolated on LB plates containing 40 μg/ml kanamycin. Roughly 200-400 transformants were obtained per plate. All colonies were pooled in a total of 1.5 ml of L-broth. Cells were washed and diluted 1:5 in saline. Cells were then selected which were capable of growth on plates containing the toxic amino acid analogs β-b 2-thienylalanine or 3-fluoro-tyrosine. Specifically, 100 μl aliqouts of washed cells were plated on each of the following growth media:

1) M9 minimal medium, 0.5% glucose, 40 μg/ml kanamycin and 10 mM β-2-thienylalanine (a toxic analog of L-phenylalanine).
2) M9 minimal medium, 0.5% glucose, 40 μg/ml kanamycin and 20 mM β-2-thienylalanine.
3) M9 minimal medium, 0.5% glucose, 40 μg/ml kanamycin and 1 mM 3-Fluorotyrosine.

Several thousand colonies were obtained on the plate containing 10 mM β-2-thienylalanine. Several were assayed and showed low levels of feedback inhibition resistance. These were not examined further. Twenty colonies were obtained on the plate containing 3-fluorotyrosine. Four of these were examined also showing low levels of feedback inhibition resistance. These were not examined further. Four colonies were obtained on the plate containing 20 mM β-2-thienylalanine. Each of these produced CMPD with very high levels of feedback inhibition resistance to L-phenylalanine. Plasmid DNA was isolated from each and used to retransform fresh competent cells of HW1012.

Cells re-transformed with plasmids from each of the four colonies were able to grow when streaked onto plates of M9 minimal medium, 0.5% glucose, 40 μg/ml kanamycin and 20 mM β-2-thienylalanine. Re-transformants also produced CMPD with levels of feedback inhibition resistance to L-phenylalanine corresponding to that of the original isolates. Plasmid DNA was then isolated from each re-transformant and characterized to determine the nature of the mutations within the pheA gene. The four mutant plasmids were designated pJN305, pJN306, pJN307 and pJN308.

EXAMPLE 2

Resistance to phenylalanine feedback inhibition for the presumptive CMPD analogs encoded by the four mutagenized, plasmid-borne CMPD DNA sequences was analyzed and compared to that of the wild type CMPD product of pheA gene expression as follows.

Preparation of Cell Extracts

To isolate enzyme for CMPD assay, a 25 ml volume of cells of HW1012 containing either pJN302, pJN305, pJN306, pJN307 or pJN308 were grown to an optical density (O.D.) of approximately 1.0 in L-broth medium containing 40 μg/ml kanamycin. Cells were recovered by centrifugation, washed in 10 mls of 200 mM Tris at pH 8, and resuspended in 1 ml of 200 mM Tris pH8. Cells were then lysed in a French pressure cell. The lysate was centrifuged for 15 minutes at 14k rpm and the supernate retained for assay. For the PD assay 50 μl of supernate were used, and for the CM assay 20 μl were employed.

PD Assay Procedure

PD activity was assayed in 1.25 ml reaction mixtures containing 27 mM Tris at pH 8, 1 mM potassium prephenate, 50 μl of cell extract to be assayed and various concentrations of L-phenylalanine as shown in Table 1. Reactions were started by the addition of the prephenate. The reaction was incubated 37° C. for 1 minute at which point a 0.25 ml sample was removed and mixed with 0.75 ml of 1M NaOH. The absorbance was then measured at 320 nm against a water blank. Further samples were removed at 5 and 9 minutes and treated identically.

The rate of increase in absorbance at 320 nm was calculated and corrected for any control rate in the absence of extract. A unit of PD activity is defined as the quantity of enzyme that catalyses the conversion of 1.0 μmole of prephenate to phenyl pyruvate in one minute under assay conditions using $17,500 M^{-1} cm^{-1}$ as the extinction coefficient for phenylpyruvate.

PD activity is shown in Table 1 in Units/ml extract and as a percentage of the activity determined in the absence of L-phenylalanine.

TABLE 1

| Phe Conc. mM | Prephenate Dehydratase Activity in Units/ml (% retained) | | | | |
|---|---|---|---|---|---|
| | Wild Type pJN302 | pJN305 | pJN306 | pJN307 | pJN308 |
| 0 | 0.61 (100%) | 0.28 (100%) | 0.39 (100%) | 0.62 (100%) | 0.34 (100%) |
| 2 | 0.1 (16%) | 0.33 (118%) | 0.34 (87%) | 0.68 (110%) | 0.33 (97%) |
| 10 | 0.035 (5.7%) | 0.3 (107%) | 0.4 (102%) | 0.63 (102%) | 0.32 (94%) |
| 20 | 0.032 (5.2%) | 0.27 (96%) | 0.36 (92%) | 0.66 (106%) | 0.31 (91%) |
| 50 | 0.029 (4.7%) | 0.23 (82%) | 0.22 (56%) | 0.6 (97%) | 0.28 (82%) |
| 100 | 0.023 (3.8%) | 0.24 (86%) | 0.1 (26%) | 0.57 (92%) | 0.26 (76%) |
| 200 | 0.026 (4.2%) | 0.2 (71%) | 0.076 (19%) | 0.52 (84%) | 0.26 (76%) |

CM Assay Procedure

CM activity was assayed in 0.8 ml reaction mixtures containing 1 mM chorismate, 100 mM Tris at pH 7.5, 0.5 mM EDTA, 0.01% BSA, 20 μl of cell extract to be assayed and varying concentrations of L-phenylalanine as shown in Table 2.

Reactions were started by addition of the cell extract. Reactions were incubated for 5 minutes at 37° C. at which point they were terminated by addition of 0.1 ml of 4.5M HCl. Reactions were incubated a further 10 minutes at 37° C. to convert all prephenate to phenyl pyruvate at which point 0.1 ml of 12M NaOH was added and the absorbance measured at 320 nm. Blanks were included which lacked only the cell extract in order to correct for substrate absorbance. Values were also corrected for CM activity due to host CM/prephenate dehydrogenase. All assays were performed in duplicate and the average values are shown. A unit is defined as the quantity of enzyme which catalyses the conversion of 1.0 μmole of chorismate to prephenate in 1 minute under the assay conditions. The extinction coefficient is as for the PD assay.

CM activity is shown in Table 2 in Units/ml extract and as a percentage of the activity determined in the absence of L-phenylalanine.

TABLE 2

| Phe Conc mM | Chorismate Mutase Activity in Units/ml (% retained) | | | | |
|---|---|---|---|---|---|
| | Wild Type pJN302 | pJN305 | pJN306 | pJN307 | pJN308 |
| 0 | 0.944 (100%) | 0.838 (100%) | 0.878 (100%) | 0.646 (100%) | 0.555 (100%) |
| 10 | 0.712 (75%) | 0.924 (110%) | 0.961 (109%) | 0.722 (119%) | 0.643 (116%) |
| 50 | 0.741 (78%) | 0.706 (84%) | 0.546 (62%) | 0.541 (84%) | 0.455 (82%) |
| 100 | 0.672 (71%) | 0.649 (77%) | 0.440 (50%) | 0.409 (63%) | 0.478 (86%) |

Tables 1 and 2 clearly indicate that both prephenate dehydratase (PD) and chorismate mutase (CM) activities of the wild type enzyme are inhibited by L-phenylalanine, with PD activity nearly totally inhibited by low levels (10 mM) and CM not inhibited by more than about 30%, even at high (100 mM) levels. This is consistent with results of studies of microbial fermentation production of phenylalanine which indicate substantial accumulation of the PD substrate, prephenate, when levels of L-phenylalanine reach 50–100 mM without substantial accumulation of the CM substrate, chorismate. Correspondingly, while resistance to inhibition of PD activity for the CMPD analog expression products was quite pronounced, resistance to inhibition of CM activity was not as dramatic. It is interesting to note, however, that low phenylalanine concentration (10 mM) invariably provided a fair degree of activation of CM activity for the analogs—a result not previously reported for the wild type enzyme.

EXAMPLE 3

Subclone analysis of plasmids pJN305, pJN306, pJN307 and pJN308 revealed that a 221 base pair AlwNI/NcoI restriction fragment (embracing codons for CMPD residues 266 through 337 of the wild type enzyme) obtained from each of the plasmids could replace the AlwNI to NcoI fragment of pJN302 and that the resulting plasmids would allow for expression of the corresponding phenylalanine inhibition resistant CMPD activity. Complete sequencing of pJN305 revealed no mutations outside the region specifying CMPD residues 301 through 315.

DNA sequence analysis of each of the four AlwNI/NcoI fragments derived from these fragments revealed no alterations in the DNA sequence outside of the region containing codons specifying CMPD residues 301 through 315. Table 3 below sets out the nucleotide and deduced amino acid sequence of pJN302 (wild type) and those of pJN305, pJN306, pJN307, pJN308 in these regions.

ing to the present invention is the strain designated AG077, an E. coli strain transformed with pJN307.

It is apparent from the information provided in Table 3 that each of the initially prepared CMPD analogs specifically differs from the wild type in only a small region embracing residues 304–310. The DNAs of plasmids pJN306 and pJN308 respectively specify the substitution analogs [Leu$^{306}$]CMPD and [Cys$^{309}$]CMPD; plasmid pJN305 specifies the deletion analog [des-Gln$^{307}$, des-Ala$^{308}$, des-Gly$^{309}$, des-Ala$^{310}$]CMPD; and plasmid pJN307 specifies the combination deletion and substitution analog [des-Thr$^{304}$, Lys$^{305}$, des-Gln$^{306}$]CMPD.

As previously indicated, while chemical mutation of a plasmid-borne pheA gene constituted the initial means for obtaining certain preferred DNA sequences of the invention, information developed through sequencing of specific mutated clones of the above Examples readily allows both the duplication of the mutated sequences (by site directed mutagenesis of pheA gene copies or chemical synthesis of all or part of the pheA gene) and the development of other analog-encoding DNAs. It is noteworthy, for example, that the DNA region specifying residues 301 to 315 of CMPD is contained within 221 base pair restriction fragment generated upon digestion of the pheA gene with AlwNI and NcoI endonucleases. This fragment thus developed may readily be synthesized to include unique restriction endonuclease digestion sites more closely adjacent the codons specifying CMPD residues 301–315 and the synthetic fragment could be employed to replace a natural sequence AlwNI/NcoI fragment in the pheA gene. Thereafter, "cassette" format mutagenesis employing short synthetic DNA duplexes may readily be employed. Potentially the emergent polymerase chain reaction (PCR) technology may be used to develop phenylalanine and phenylalanine derivative feedback inhibition resistant analog-encoding sequences of the invention.

Numerous modifications and variations in the inven-

TABLE 3

| pJN302 | 301 | 302 | 303 | 304 | 305 | 306 | 307 | 308 | 309 | 310 | 311 | 312 | 313 | 314 | 315 |
|---|---|---|---|---|---|---|---|---|---|---|---|---|---|---|---|
| | TTA | ATG | GCG | ACC | GGG | CAA | CAA | GCC | GGT | GCG | CTG | GTT | GAA | GCG | TTG |
| | Leu | Met | Ala | Thr | Gly | Gln | Gln | Ala | Gly | Ala | Leu | Val | Glu | Ala | Leu |
| pJN305 | 301 | 302 | 303 | 304 | 305 | 306 | 307 | 308 | 309 | 310 | 311 | 312 | 313 | 314 | 315 |
| | TTA | ATG | GCG | ACC | GGG | CAG | | | | | CTG | GTT | GAA | GCG | TTG |
| | Leu | Met | Ala | Thr | Gly | Gln | — | — | — | — | Leu | Val | Glu | Ala | Leu |
| pJN306 | 301 | 302 | 303 | 304 | 305 | 306* | 307 | 308 | 309 | 310 | 311 | 312 | 313 | 314 | 315 |
| | TTA | ATG | GCG | ACC | GGG | CTA | CAA | GCC | GGT | GCG | CTG | GTT | GAA | GCG | TTG |
| | Leu | Met | Ala | Thr | Gly | Leu | Gln | Ala | Gly | Ala | Leu | Val | Glu | Ala | Leu |
| pJN307 | 301 | 302 | 303 | 304 | 305 | 306 | 307 | 308 | 309 | 310 | 311 | 312 | 313 | 314 | 315 |
| | TTA | ATG | GCG | | AAA | | CAA | GCC | GGT | GCG | CTG | GTT | GAA | GCG | TTG |
| | Leu | Met | Ala | — | Lys | — | Gln | Ala | Gly | Ala | Leu | Val | Glu | Ala | Leu |
| pJN308 | 301 | 302 | 303 | 304 | 305 | 306 | 307 | 308 | 309* | 310 | 311 | 312 | 313 | 314 | 315 |
| | TTA | ATG | GCG | ACC | GGG | CAA | CAA | GCC | TGT | GCG | CTG | GTT | GAA | GCG | TTG |
| | Leu | Met | Ala | Thr | Gly | Gln | Gln | Ala | Cys | Ala | Leu | Val | Glu | Ala | Leu |

The host strain which is currently preferred as providing the best titres with a mutant pheA gene according to as above described with respect to preferred embodiments are expected to occur to those skilled in the art. Therefore, only such limitations as appear in the appended claims should be placed thereon.

What is claimed is:

1. DNA encoding *E. coli* [des-Gln$^{307}$, des-Ala$^{308}$, des-Gly$^{309}$, des-Ala$^{310}$]CMPD wherein CMPD is exemplified by Met-Thr-Ser-Glu-Asn-Pro-Leu-Leu-Ala-Leu-Arg-Glu-Lys-Ile-Ser-Ala- Leu-Asp-Glu-Lys-Leu-Leu-Ala-Leu-Leu-Ala-Glu-Arg-Arg-Glu-Leu-Ala-Val-Glu-Val-Gly-Lys-Ala-Lys-Leu-Leu-Ser-His-Arg-Pro-Val-Arg-Asp-Ile-Asp-Arg-Glu-Arg-Asp-Leu-Leu-Glu-Arg-Leu-Ile-Thr-Leu-Gly-Lys-Ala-His-His-Leu-Asp-Ala0His-Tyr-Ile-Thr-Arg-Leu-Phe-Gln-Leu-Ile-Ile-Glu-Asp-Ser-Val-Leu-Thr-Gln-Gln-Ala-Leu-Leu-Gln-Gln-His-Leu-Asn-Lys-Ile-Asn-Pro-His-Ser-Ala-Arg-Ile-Ala-Phe-Leu-Gly-Pro-Lys-Gly-Ser-Tyr-Ser-His-Leu-Ala-Ala-Arg-Gln-Tyr-Ala-Ala-Arg-His-Phe-Glu-Gln-Phe-Ile-Glu-Ser-Gly-Cyc-Ala-Lys-Phe-Ala-Asp-Ile-Phe-Asn-Gln-Val-Glu-Thr-Gly-Gln-Ala-Asp-Tyr-Ala-Val-Val-Pro-Ile-Glu-Asn-Thr-Ser-Ser-Gly-Ala-Ile-Asn-Asp-Val-Tyr-Asp-Leu-Leu-Gln-His-Thr-Ser-Leu-Ser-Ile-Val-Gly-glu-Met-Thr-Leu-Thr-Ile-Asp-His-Cys-Leu-Leu-Val-Ser-Gly-Thr-Thr-Asp-Leu-Ser-Thr-Ile-Asn-Thr-Val-Tyr-Ser-His-Pro-Gln-Pro-Phe-Gln-Gln-Cys-Ser-Lys-Phe-Leu-Asn-Arg-tyr-Pro-His-Trp-Lys-Ile-Glu-Tyr-Thr-Glu-Ser-Thr-Ser-Ala-Ala-Met-Glu-Lys-Val-Ala-Gln-Ala-Lys-Ser-Pro-His-Val-Ala-Ala-Leu-Gly-Ser-Glu-Ala-Gly-Gly-Thr-Leu-Tyr-Gly-Leu-Gln-Val-Leu-Glu-Arg-Ile-Glu-Ala-Asn-Gln-Arg-Gln-Asn-Phe-Thr-Arg-Phe-Val-Val-Leu-Ala-Arg-Lys-Ala-Ile-Asn-Val-Ser-Asp-Gln-Val-Pro-Ala-Lys-Thr-Thr-Leu-Leu-Met-Ala-Thr-Gly-Gln-Gln-Ala-Gly-Ala-Leu-Val-Glu-Ala-Leu-Leu-Val-Leu-Arg-Asn-His-Asn-Leu-Ile-Met-Thr-Arg-Leu-Glu-Ser-Arg-Pro-Ile-His-Gly-Asn-Pro-Trp-Glu-Glu-Met-Phe-Tyr-Leu-Asp-Ile-Gln-Ala-Asn-Leu-Glu-Ser-Ala-Glu-Met-Gln-Lys-Ala-Leu-Lys-Glu-Leu-Gly-Glu-Ile-Thr-Arg-Ser-Met-Lys-Val-Leu-Gly-Cys-Tyr-Pro-Ser-Glu-Asn-Val-Val-Pro-Val-Asp-Pro-Thr.

2. DNA encoding *E. coli* [Leu$^{306}$]CMPD wherein CMPD is exemplified by Met-Thr-Ser-Glu-Asn-Pro-Leu-Leu-Ala-Leu-Arg-Glu-Lys-Ile-Ser-Ala- Leu-Asp-Glu-Lys-Leu-Leu-Ala-Leu-Leu-Ala-Glu-Arg-Arg-Glu-Leu-Ala-Val-Glu-Val-Gly-Lys-Ala-Lys-Leu-Leu-Ser-His-Arg-Pro-Val-Arg-Asp-Ile-Asp-Arg-Glu-Arg-Asp-Leu-Leu-Glu-Arg-Leu-Ile-Thr-Leu-Gly-Lys-Ala-His-His-Leu-Asp-Ala-His-Tyr-Ile-Thr-Arg-Leu-Phe-Gln-Leu-Ile-Ile-Glu-Asp-Ser-Val-Leu-Thr-Gln-Gln-Ala-Leu-Leu-Gln-Gln-His-Leu-Asn-Lys-Ile-Asn-Pro-His-Ser-Ala-Arg-Ile-Ala-Phe-Leu-Gly-Pro-Lys-Gly-Ser-Tyr-Ser-His-Leu-Ala-Ala-Arg-Gln-Tyr-Ala-Ala-Arg-His-Phe-Glu-Gln-Phe-Ile-Glu-Ser-Gly-Cys-Ala-Lys-Phe-Ala-Asp-Ile-Phe-Asn-Gln-Val-Glu-Thr-Gly-Gln-Ala-Asp-Tyr-Ala-Val-Val-Pro-Ile-Glu-Asn-Thr-Ser-Ser-Gly-Ala- Ile-Asn-Asp-Val-Tyr-Asp-Leu-Leu-Gln-His-Thr-Ser-Leu-Ser-Ile-Val-Gly-Glu-Met-Thr-Leu-Thr-Ile-Asp-His-Cys-LeuLeu-Val-Ser-Gly-Thr-Thr-Asp-Leu-Ser-Thr-Ile-Asn-Thr-Val-Tyr-Ser-His-Pro-Gln-Pro-Phe-Gln-Gln-Cys-Ser-Lys-Phe-Leu-Asn-Arg-Tyr-Pro-His-Trp-Lys-Ile-Glu-Tyr-Thr-Glu-Ser-Thr-Ser-Ala-Ala-Met-Glu-Lys-Val-Ala-Gln-Ala-Lys-Ser-Pro-His-Val-Ala-Ala-Leu-Gly-Ser-Glu-Ala-Gly-Gly-Thr-Leu-Tyr-Gly-Leu-Gln-Val-Leu-Glu-Arg-Ile-Glu-Ala-Asn-Gln-Arg-Gln-Asn-Phe-Thr-Arg-Phe-Val-Val-Leu-Ala-Arg-Lys-Ala-Ile-Asn-Val-Ser-Asp-Gln-Val-Pro-Ala-Lys-Thr-Thr-Leu-Leu-Met-Ala-Thr-Gly-Gln-Gln-Ala-Gly-Ala-Leu-Val-Glu-Ala-Leu-Leu-Val-Leu-Arg-Asn-His-Asn-Leu-Ile-Met-Thr-Arg-Leu-Glu-Ser-Arg-Pro-Ile-His-Gly-Asn-Pro-Trp-Glu-Glu-Met-Phe-Tyr-Leu-Asp-Ile-Gln-Ala-Asn-Leu-Glu-Ser-Ala-Glu-Met-Gln-Lys-Ala-Leu-Lys-Glu-Leu-Gly-Glu-Ile-Thr-Arg-Ser-Met-Lys-Val-Leu-Gly-Cys-Tyr-Pro-Ser-Glu-Asn-Val-Val-Pro-Val-Asp-Pro-Thr.

3. DNA encoding *E. coli* [des-Thr$^{304}$, Lys$^{305}$, des-Gln$^{306}$]CMPD wherein CMPD is exemplifeid by Met-Thr-Ser-Glu-Asn-Pro-Leu-Leu-Ala-Leu-Arg-Glu-Lys-Ile-Ser-Ala-Leu-Asp-Glu-Lys-Leu-Leu-Ala-Leu-Leu-Ala-Glu-Arg-Arg-Glu-Leu-Ala-Val-Glu-Val-Gly-Lys-Ala-Lys-Leu-Leu-Ser-His-Arg-Pro-Val-Arg-Asp-Ile-Asp-ARg-Glu-Arg-Asp-Leu-Leu-Glu-Arg-Leu-Ile-Thr-Leu-Gly-Lys-Ala-His-His-Leu-Asp-Ala-His-Tyr-Ile-Thr-ARg-Leu-Phe-Gln-Leu-Ile-Ile-Glu-Asp-Ser-Val-Leu-Thr-Gln-Gln-Ala-Leu-Leu-Gln-Gln-His-Leu-Asn-Lys-Ile-Asn-ProHis-Ser-Ala-Arg-Ile-Ala-Phe-Leu-Gly-Pro-Lys-Gly-Ser-Tyr-Ser-His-Leu-Ala-Ala-Arg-Gln-Tyr-Ala-Ala-Arg-His-Phe-Glu-Gln-Phe-Ile-Glu-Ser-Gly-Cys-Ala-Lys-Phe-Ala-Asp-Ile-Phe-Asn-Gln-Val-Glu-Thr-Gly-Gln-Ala-Asp-Tyr-Ala-Val-Val-Pro-Ile-Glu-Asn-Thr-Ser-Ser-Gly-Ala-Ile-Asn-Asp-Val-Tyr-Asp-Leu-Leu-Gln-His-Thr-Ser-Leu-Ser-Ile-Val-Gly-Glu-Met-Thr-Leu-Thr-Ile-Asp-His-Cys-Leu-Leu-Val-Ser-Gly-Thr-Thr-Asp-Leu-Ser-Thr-Ile-Asn-Thr-Val-Tyr-Ser-His-Pro-Gln-Pro-Phe-Gln-Gln-Cys-Ser-Lys-Phe-Leu-Asn-Arg-Tyr-Pro-His-Trp-Lys-Ile-Glu-Tyr-Thr-Glu-Ser-Thr-Ser-Ala-Ala-Met-Glu-Lys-Val-Ala-Gln-Ala-Lys-Ser-Pro-His-Val-Ala-Ala-Leu-Gly-Ser-Glu-Ala-Gly-Gly-Thr-Leu-Tyr-Gly-Leu-Gln-Val-Leu-Glu-Arg-Ile-Glu-Ala-Asn-Gln-Arg-Gln-Asn-Phe-Thr-Arg-Phe-Val-Val-Leu-Ala-Arg-Lys-Ala-Ile-Asn-Val-Ser-Asp-Gln-Val-Pro-Ala-Lys-Thr-Thr-Leu-Leu-Met-Ala-Thr-Gly-Gln-Gln-Ala-Gly-Ala-Leu-Val-Glu-Ala-Leu-Leu-Val-Leu-Arg-Asn-His-Asn-Leu-Ile-Met-Thr-Arg-Leu-Glu-Ser-Arg-Pro-Ile-His-Gly-Asn-Pro-Trp-Glu-Glu-Met-Phe-Tyr-Leu-Asp-Ile-Gln-Ala-Asn-Leu-Glu-Ser-Ala-Glu-Met-Gln-Lys-Ala-Leu-Lys-Glu-Leu-Gly-Glu-Ile-Thr-Arg-Ser-Met-Lys-Val-Leu-Gly-Cys-Tyr-Pro-Ser-Glu-Asn-Val-Val-Pro-Val-Asp-Pro-Thr.

4. DNA encoding *E. coil* [Cys$^{309}$]CMPD wherein CMPD is exemplified by Met-Thr-Ser-Glu-Asn-Pro-Leu-Leu-Ala-Leu-Arg-Glu-Lys-Ile-Ser-Ala-Leu-Asp-Glu-Lys-Leu-Leu-Ala-Leu-Leu-Ara-Glu-Arg-Arg-Glu-Leu-Ala-Val-Glu-Val-Gly-Lys-Ala-Lys-Leu-Leu-Ser-His-Arg-Pro-Val-Arg-Asp-Ile-Asp-Arg-Glu-Arg-Asp-Leu-Leu-Glu-Arg-Leu-Ile-Thr-Leu-Gly-Lys-Ala-His-His-Leu-Asp-Ala-His-Tyr-Ile-Thr-Arg-Leu-Phe-Gln-Leu-Ile-Ile-Glu-Asp-Ser-Val-Leu-Thr-Gln-Gln-Ala-Leu-Leu-Gln-Gln-His-Leu-Asn-Lys-Ile-Asn-Pro-His-Ser-Ala-Arg-Ile-Ala-Phe-Leu-Gly-Pro-Lys-Gly-Ser-Tyr-Ser-His-Leu-Ala-Ala-Arg-Gln-Tyr-Ala-Ala-Arg-His-Phe-Glu-Gln-Phe-Ile-Glu-Ser-Gly-Cys-Ala-Lys-Phe-Ala-Asp-Ile-Phe-AsnGln-Val-Glu-Thr-Gly-Gln-Ala-Asp-Tyr-Ala-Val-Val-Pro-Ile-Glu-Asn-Thr-Ser-Ser-Gly-Ala-Ile-Asn-Asp-Val-Tyr-Asp-Leu-Leu-Gln-His-Thr-Ser-Leu-Ser-Ile-Val-Gly-Glu-Met-Thr-Leu-Thr-Ile-Asp-His-Cys-Leu-Leu-Val-Ser-Gly-Thr-Thr-Asp-Leu-Ser-Thr-Ile-Asn-Thr-Val-Tyr-Ser-His-Pro-Gln-Pro-Phe-Gln-Gln-Cys-Ser-Lys-Phe-Leu-Asn-Arg-Tyr-Pro-His-Trp-Lys-Ile-Glu-Tyr-Thr-Glu-Ser-Thr-Ser-Ala-Ala-Met-Glu-Lys-Val-Ala-Gln-Ala-Lys-Ser-Pro-His-Val-Ala-Ala-Leu-Gly-Ser-Glu-Ala-Gly-Gly-Thr-Leu-Tyr-Gly-Leu-Gln-Val-Leu-Glu-Arg-Ile-Glu-Ala-Asn-Gln-Arg-Gln-Asn-Phe-Thr-Arg-Phe-Val-Val-Leu-Ala-Arg-Lys-Ala-Ile-Asn-Val-Ser-Asp-Gln-Val-Pro-ala-Lys-Thr-Thr-Leu-Leu-Met-Ala-Thr-Gly-Gln-Gln-Ala-Gly-Ala-Leu-Val-Glu-Ala-Leu-Leu-Val-Leu-Arg-Asn-His-Asn-Leu-Ile-Met-Thr-Arg-Leu-Glu-Ser-Arg-Pro-Ile-His-Gly-Asn-Pro-Trp-Glu-Glu-Met-Phe-Tyr-Leu-Asp-Ile-Gln-Ala-Asn-Leu-Glu-Ser-Ala-Glu-Met-Gln-Lys-Ala-Leu-Lys-Glu-Leu-Gly-Glu-Ile-Thr-Arg-Ser-Met-Lys-Val-Leu-Gly-Cys-Tyr-Pro-Ser-Glu-Asn-Val-Val-Pro-Val-Asp-Pro-Thr.

* * * * *

UNITED STATES PATENT AND TRADEMARK OFFICE
CERTIFICATE OF CORRECTION

PATENT NO. : 5,120,837
DATED : June 9, 1992
INVENTOR(S) : FOTHERINGHAM, Ian G. and Nelms, Jennifer It is certified that error appears in the above-identified patent and that said Letters Patent is hereby corrected as shown below:

Column 9, line 2, please replace "AlaOHis-" with -- Ala-His- --.

Column 9, line 16, please replace "Cyc-" with -- Cys- --.

Column 9, line 54, please replace "LeuLeu-" with -- Leu-Leu- --.

Column 10, line 8, please replace "ARg-" with -- Arg- --.

Column 10, line 11, please replace "ARg-" with -- Arg- --.

Column 10, line 13, please replace "ProHis-" with -- Pro-His --.

Column 10, line 38, please replace "Ara-" with -- Ala- --.

Column 10, line 48, please replace "AsnGln-" with -- Asn-Gln- --.

Column 10, line 61, please replace "ala-" with -- Ala- --.

Signed and Sealed this

Third Day of August, 1993

*Attest:*

MICHAEL K. KIRK

*Attesting Officer*     Acting Commissioner of Patents and Trademarks